United States Patent
Rapoport et al.

(10) Patent No.: US 7,186,221 B2
(45) Date of Patent: Mar. 6, 2007

(54) POSITIVE AIRWAY PRESSURE SYSTEM AND METHOD FOR TREATMENT OF SLEEPING DISORDER IN PATIENT

(75) Inventors: David M. Rapoport, New York, NY (US); Robert G. Norman, New Windsor, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 11/210,568

(22) Filed: Aug. 24, 2005

(65) Prior Publication Data
US 2006/0009708 A1  Jan. 12, 2006

Related U.S. Application Data

(63) Continuation of application No. 10/642,459, filed on Aug. 14, 2003, now Pat. No. 6,988,994.

(51) Int. Cl.
*A61B 5/08* (2006.01)
*A61M 16/00* (2006.01)

(52) U.S. Cl. ............ 600/538; 128/204.23; 128/204.18; 128/204.26; 600/529

(58) Field of Classification Search ................ 600/529, 600/531–538; 128/200.24, 204.18, 204.21, 128/204.22, 204.23, 204.26
See application file for complete search history.

(56) References Cited

U.S. PATENT DOCUMENTS

| | | | |
|---|---|---|---|
| 5,492,113 A * | 2/1996 | Estes et al. ............ | 128/204.23 |
| 5,522,382 A * | 6/1996 | Sullivan et al. ........ | 128/204.23 |
| 6,171,258 B1 * | 1/2001 | Karakasoglu et al. ....... | 600/529 |
| 6,363,933 B1 * | 4/2002 | Berthon-Jones ........ | 128/204.23 |
| 6,367,474 B1 * | 4/2002 | Berthon-Jones et al. ............ | 128/204.23 |
| 6,397,845 B1 * | 6/2002 | Burton .................. | 128/204.23 |
| 6,398,739 B1 * | 6/2002 | Sullivan et al. ............. | 600/529 |
| 6,409,676 B2 * | 6/2002 | Ruton et al. ................. | 600/532 |
| 6,988,994 B2 * | 1/2006 | Rapoport et al. ........... | 600/538 |
| 2002/0185130 A1 * | 12/2002 | Wright et al. .......... | 128/204.21 |

FOREIGN PATENT DOCUMENTS

WO  WO 2094358 A1 * 11/2002

* cited by examiner

*Primary Examiner*—Charles A Marmor, II
*Assistant Examiner*—Navin Natnithithadha
(74) *Attorney, Agent, or Firm*—Fay Kaplun & Marcin, LLP.

(57) ABSTRACT

Described are a positive airway pressure system and method for treatment of a sleeping disorder in a patient. The system includes a generator, a sensor and a processing arrangement. The generator supplies airflow and applies a pressure at to an airway of a patient. The sensor measures data corresponding to patient's breathing patterns. The processing arrangement analyzes the breathing patterns to determine whether the breathing patterns are indicative of at least one of the following patient's states: (i) a regular breathing state, (ii) a sleep disorder breathing state, (iii) a REM sleep state and (iv) a troubled wakefulness state. The processing arrangement adjusts the applied pressure as a function of the patient's state.

16 Claims, 3 Drawing Sheets

POSITIVE AIRWAY PRESSURE SYSTEM AND METHOD FOR TREATMENT OF SLEEPING DISORDER IN PATIENT

This application is a Continuation of U.S. patent application Ser. No. 10/642,459, entitled "Positive Airway Pressure System and Method for Treatment of Sleeping Disorder in Patient" filed Aug. 14, 2003 now U.S. Pat. No. 6,988,994. The specification of the above-identified parent application is incorporated herewith by reference.

BACKGROUND

Obstructive sleep apnea syndrome (OSAS) is a well recognized disorder which may affect as much as 1–5% of the adult population. OSAS is one of the most common causes of excessive daytime somnolence. OSAS is most frequent in obese males, and it is the single most frequent reason for referral to sleep disorder clinics.

OSAS is associated with many conditions in which there is an anatomic or functional narrowing of the patient's upper airway, and is characterized by an intermittent obstruction of the upper airway occurring during sleep. The obstruction results in a spectrum of respiratory disturbances ranging from the total absence of airflow (apnea) to significant obstruction with or without reduced airflow (hypopnea and snoring), despite continued respiratory efforts. The morbidity of the syndrome arises from hypoxemia, hypercapnia, bradycardia and sleep disruption associated with the apneas and subsequent arousals from sleep.

The pathophysiology of OSAS has not yet been fully worked out. However, it is well recognized that obstruction of the upper airway during sleep is in part due to the collapsible behavior of the supraglottic segment of the airway resulting from negative intraluminal pressure generated by inspiratory effort. Thus, in patients suffering from OSAS, the upper airway during sleep behaves substantially as a Starling resistor (i.e., the airflow is limited to a fixed value irrespective of the driving (inspiratory) pressure). Partial or complete airway collapse may then occur with the loss of airway tone which is characteristic of the onset of sleep and which may be exaggerated in OSAS.

Since 1981, positive airway pressure (PAP) therapy applied by a tight fitting nasal mask worn during sleep has evolved as the most effective treatment for OSAS, and is now the standard of care. The availability of this non-invasive form of therapy has resulted in extensive publicity for OSAS and the appearance of large numbers of patients who previously may have avoided the medical establishment because of the fear of tracheostomy. Increasing the comfort of the PAP system has been a major goal of research aimed at improving patient compliance with the PAP therapy.

PAP therapy has become the mainstay of treatment in Obstructive Sleep Disordered Breathing (OSDB), which includes Obstructive Sleep Apnea, Upper Airway Resistance Syndrome, Snoring, exaggerations of sleep induced increases in the collapsibility of the upper airway and all conditions in which inappropriate collapsing of a segment of the upper airway causes significant un-physiologic obstruction to airflow. This collapse generally occurs whenever pressure in the collapsible portion of the airway decreases below a level defined as a "critical tissue pressure" in the surrounding wall. The PAP therapy is directed to maintaining pressure in the collapsible portion of the airway at or above the critical tissue pressure at all times. In the past, this goal has been achieved by raising a pressure delivered to the patient's airway to a level higher than this critical tissue pressure at all times when the patient is wearing the device. In general, the need for the PAP therapy occurs only during sleep. However, the conventional PAP therapy has not taken sleep/wake state into account, and conventional PAP systems apply pressure unnecessarily when the patient is awake. The applied pressure is either a constant pressure, or a pressure based on breath-by-breath determination of the need for treatment. Various strategies for determining the minimal pressure have evolved based on recognizing pathological events (e.g., apnea, hypopnea and other evidence of high airway resistance)as determined by feedback from a variety of signals that indicate the need for the PAP therapy due to the airway collapse.

Despite its success, limitations on the use of the conventional PAP systems still exist based on, for example, discomfort from the mask and the pressure required to obliterate the apneas. In particular, patients often report discomfort due to high pressure while being awake. To avoid this discomfort, the applied pressure should be provided only when the patient is asleep. For example, a "ramp" system utilizes a patient activated delay in the onset of the applied pressure, but the ramp system is not automatically responsive to patient awakenings during the night, unless deliberately activated by the patient pushing a button.

Patient's discomfort during wakefulness is often associated with changes from a regular breathing pattern (e.g., near constant breath size and frequency) to one which contains irregularities. These irregular patterns (e.g., including isolated big breaths, short pauses, and changes in breath flow shape that do not vary in any regular pattern)are recognized by inspection of the airflow tracing alone, and frequently occur when the patient is distressed by the PAP system.

Some conventional PAP systems utilize algorithms which continuously and automatically titrate the applied pressure. These algorithms depend on detecting evidence of airway collapse from the breathing signals. However, these algorithms of the conventional PAP systems have certain limitations. For example, the irregular pattern of breathing present while a subject is awake, and more so when anxious, interferes with the processing of the breath signal that calculates the applied pressure

SUMMARY OF THE INVENTION

Described are a positive airway pressure system and method for treatment of a sleeping disorder in a patient. The system includes a generator, a sensor and a processing arrangement. The generator supplies airflow and applies a pressure to an airway of a patient. The sensor measures data corresponding to a patient's breathing pattern. The processing arrangement analyzes the breathing patterns to determine whether the breathing patterns are indicative of at least one of the following patient states: (I) a regular breathing state, (ii) a sleep disorder breathing state, (iii) a REM sleep state and (iv) a troubled wakefulness state. The processing arrangement adjusts the applied pressure as a function of the patient's state. Those skilled in the art will understand that the regular breathing state will include both an apnea free sleeping and a relaxed wakeful state of the patient, while the troubled wakefulness state is one in which anxiety to discomfort of the patient results in irregular breathing.

BRIEF DESCRIPTION OF THE DRAWINGS

The accompanying drawings which are incorporated in and constitute part of the specification, illustrate an embodiment of the invention and, together with the description, serve to explain examples of the present invention. In the drawings.

DETAILED DESCRIPTION

Figure 1:
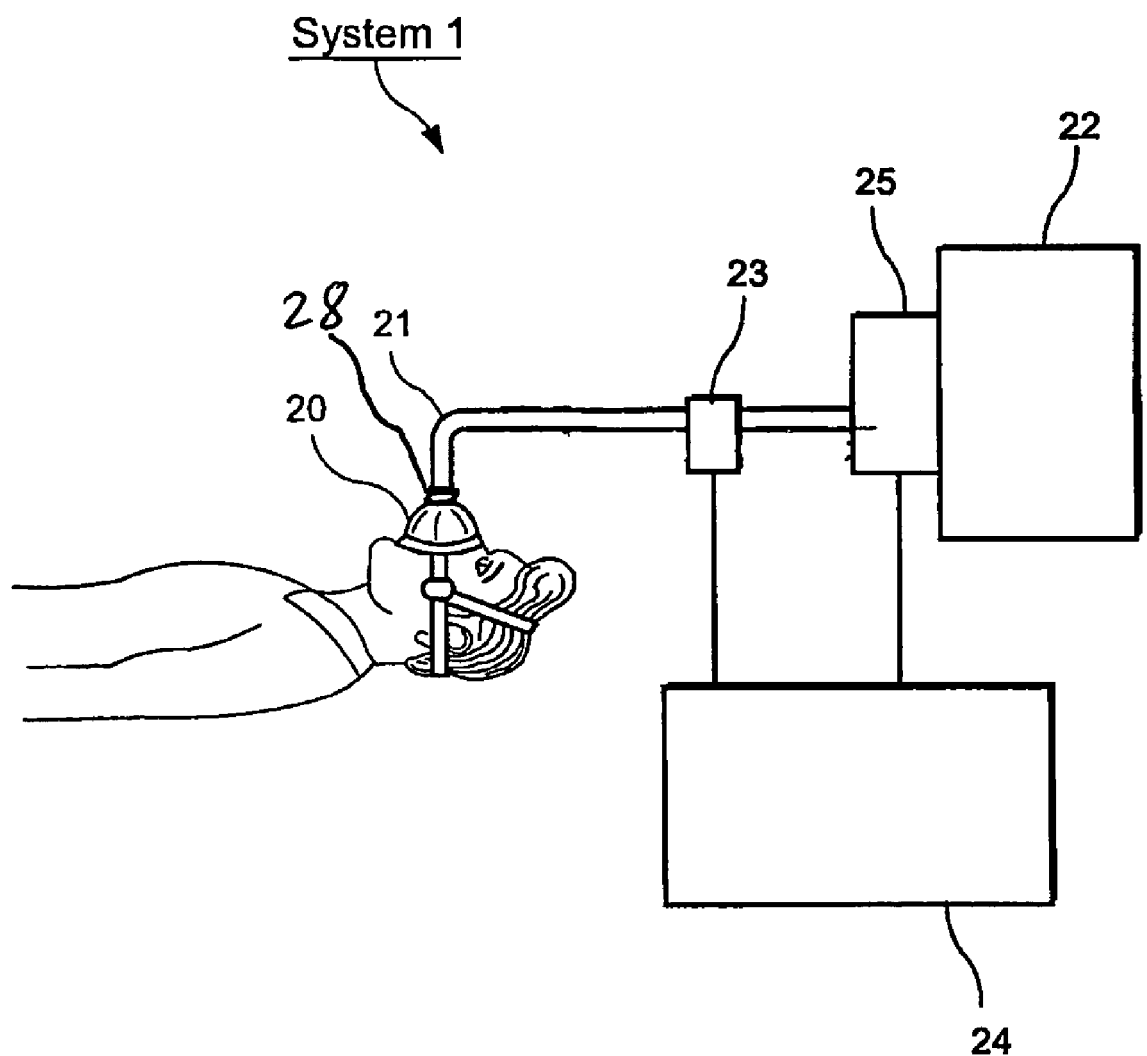
FIG. 1 shows an exemplary embodiment of a system according to the present invention.

FIG. 1 shows an exemplary embodiment of a system 1 according to the present invention. The system 1 may include a mask 20 which is connected via a tube 21 to receive airflow having a particular pressure from a flow generator 22. The amount of pressure provided to a particular patient varies depending on patient's particular condition. Such amount of pressure may be determined utilizing any conventional PAP therapy methods.

The mask 20 covers the patient's nose and/or mouth. Conventional flow sensors 23 are coupled to the tube 21. The sensors 23 detect the rate of airflow to/from patent and/or a pressure supplied to the patent by the generator 22. The sensors 23 may be internal or external to the generator 22. Signals corresponding to the airflow and/or the pressure are provided to a processing arrangement 24 for processing. The processing arrangement 24 outputs a signal to a conventional flow control device 25 to control a pressure applied to the flow tube 21 by the flow generator 22. Those skilled in the art will understand that, for certain types of flow generators which may by employed as the flow generator 22, the processing arrangement 24 may directly control the flow generator 22, instead of controlling airflow therefrom by manipulating the separate flow control device 25.

The system 1 may also include a continuous leak port or other venting arrangement 28. The venting arrangement 28 allows for gases contained in the exhaled airflow of the patient to be diverted from the incoming airflow to prevent re-breathing of the exhaled gases.

Figure 2:
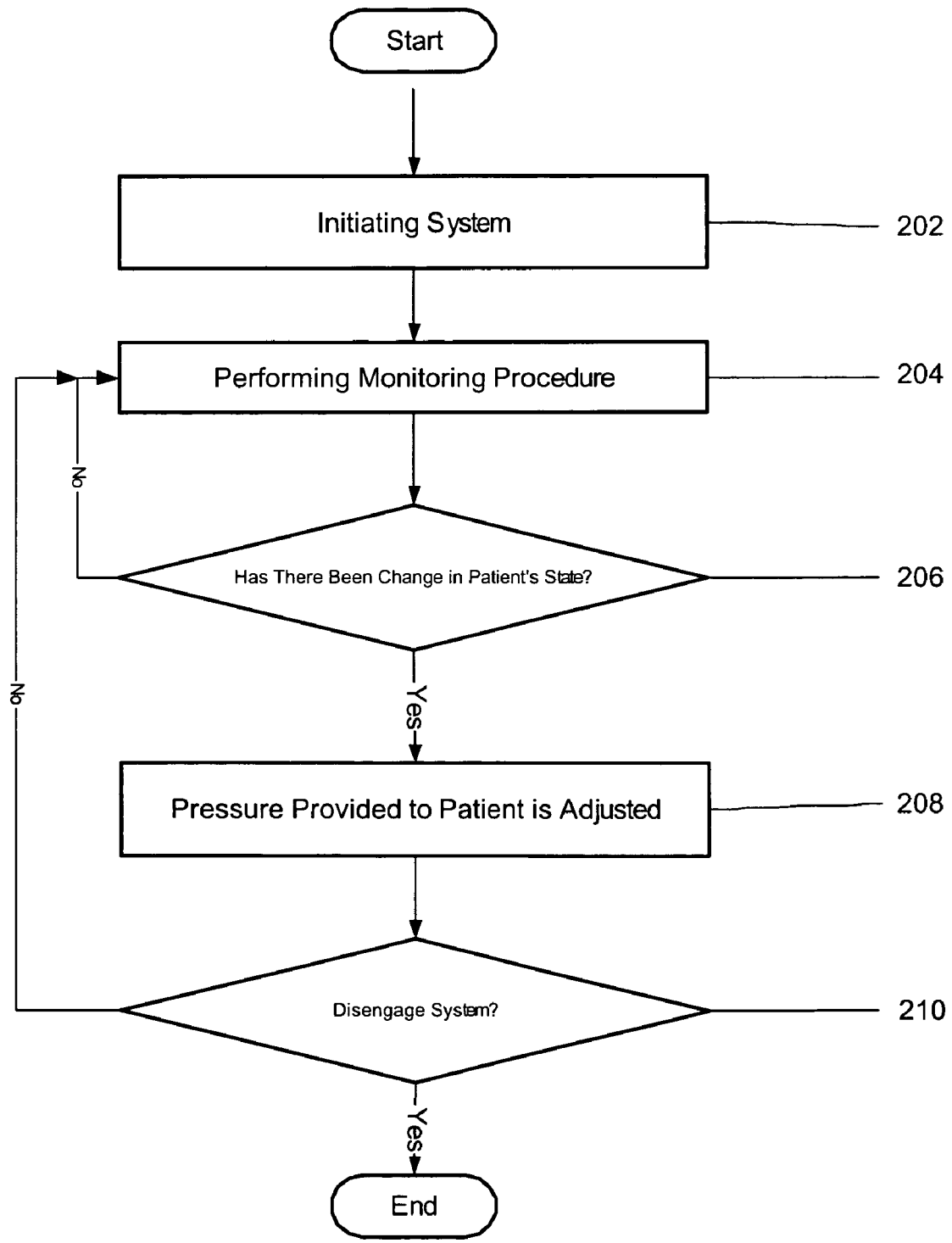
FIG. 2 shows an exemplary embodiment of a method according to the present invention which utilizes the system shown in FIG. 1.

FIG. 2 shows an exemplary embodiment of a method according to the present invention. In step 202, the patient initiates the system 1 by placing the mask 20 over his face and powering up the generator 22, the flow control device 25 and the processing arrangement 24.

In step 204, the system 1 initiates a real-time monitoring procedure of the patient's breathing patterns. The monitoring procedure is performed by the processing arrangement 24 which may utilize pre-stored patient data along with current data provided by the sensors 23 regarding the airflow to and from the patient and/or the applied pressure.

During the monitoring procedure, the processing arrangement 24 makes a determination as to a current state of the patient (e.g., whether the patient is asleep, awake and breathing regularly or awake and breathing irregularly due to distress or anxiousness). Such determination can be made based on a number of different measurements. For example, the processing arrangement 24 may analyze the patient's heart rate, blood pressure EEG data, breathing patterns, etc. in the determining the patient's state.

Figure 3:
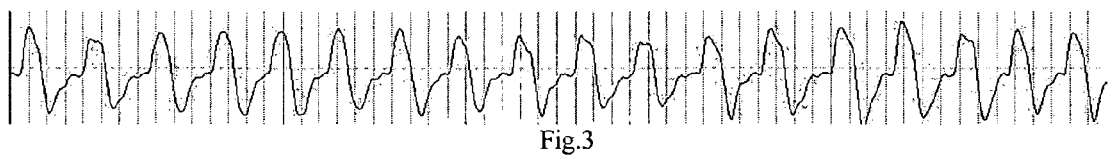
FIG. 3 shows a waveform of airflow during regular wakefulness of a patient (e.g., not anxious) who utilizes the system according to the present invention.
Figure 4:
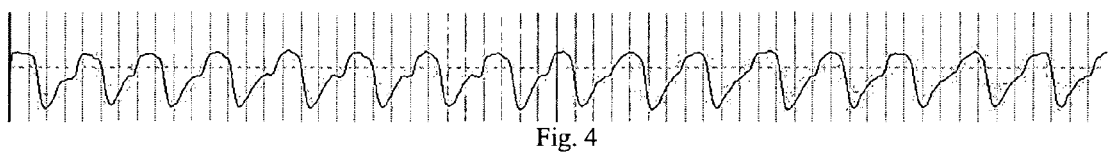
FIG. 4 shows a waveform of airflow during regular sleep in a patient.

There are a number of characteristics of the patient's breathing patterns that may be taken into account in making such a determination. FIGS. 3 and 4 show breathing patterns indicative of quiet, regular and relaxed breathing in a patient during the PAP therapy. FIG. 3 is indicative of relaxed wakefulness (patient is not anxious or distressed). FIG. 4 shows a period of relaxed breathing during sleep during which the patient is correctly treated with the PAP therapy. In either case the applied pressure can be delivered without impairing comfort. In addition, there are periods of sleep disordered breathing during which the PAP therapy must be applied. Indices of sleep disordered breathing include apnea (e.g., periods of zero airflow which are greater than 8–10 seconds alternating with large breaths), hypopnea (e.g., cyclical periods of airflow which is substantially reduced, lasting 10 or more seconds, and terminated by larger breaths), or periods of intermittent and cyclical change in the shape of the signal (e.g., characterized by flattening of the waveform, terminated by normal shaped breaths).

Figure 7:
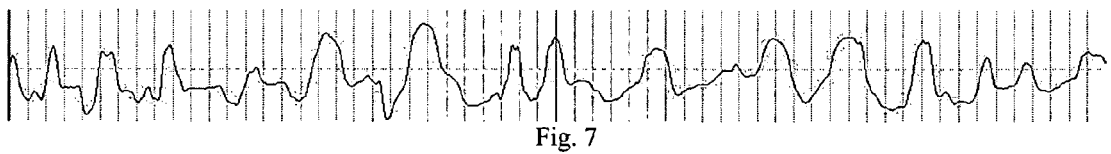
FIG. 7 shows a waveform of airflow from a patient which is indicative of a period of troubled wakefulness.

In contrast, the following exemplary characteristics may suggest that the patient is awake and anxious or distressed: pure mouth breathing (e.g., no signal from the sensors 23 which is configured to detect the patient's airflow from the nose); erratic large breaths with varying inspiratory times; irregularity of intervals between breaths (but not cyclic apneas which indicate sleep and the need for higher pressure, etc). FIG. 7 shows a period of such troubled wakefulness in which the breathing pattern is characterized by irregularly variations in the size and/or frequency of breaths and/or irregular variation in the shapes of the patient's airflow tracing indicating that the patient is awake and either anxious or uncomfortable. There is, however, no cyclical change (e.g., a periodic irregularity) in breath size, such as would be seen during apnea and hypopnea sleep events. One of the ways to increase the patient's comfort is to reduce the applied pressure when it is not needed. Patients with obstructive sleep apnea do not require any pressure at all while awake. Thus, lowering the pressure applied to the mask during such periods of irregular breathing should improve the patient's comfort until the patient falls asleep (e.g., which may be marked by the resumption of regularity or cyclical but regular periods of obstruction easily recognized as apnea and hypopnea or elevated upper airway resistance).

Figure 5:
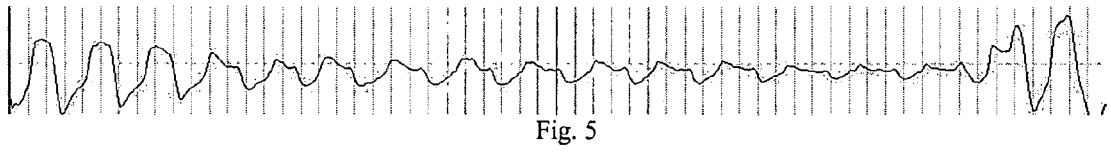
FIG. 5 shows a waveform of airflow from a sleeping patient which is indicative of an elevated upper airway pressure resistance and hypopnea.
Figure 6:
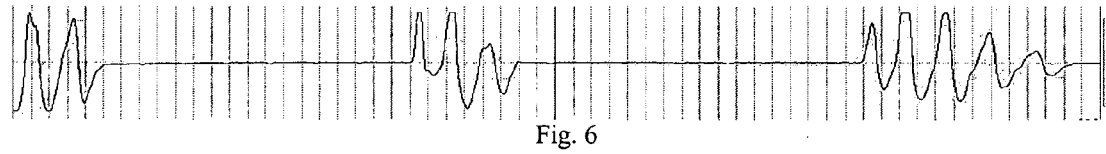
FIG. 6 shows a waveform of airflow from a sleeping patient which is indicative of a repetitive obstructive apnea.

The above-described breathing patterns are distinguishable from the slow modulation in breath size and inspiratory timing seen, e.g., in Cheyne Stoke and other forms of obstructive apnea. FIG. 5 shows a breathing pattern of a patient on the PAP therapy which includes an event of elevated upper airway resistance and hypopnea during sleep and FIG. 6 show a breathing pattern corresponding to a repetitive obstructive apnea. In both cases, the changes in breath size and frequency are slowly modulated and repetitive and cyclical (e.g., regularly irregular). In these periods, the applied pressure is either needed or must be raised, but there is no indication it is contributing to patient distress. Thus, the applied pressure should not be lowered.

Figure 8:
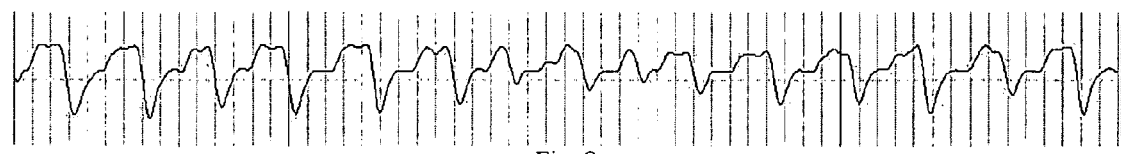
FIG. 8 shows a waveform of airflow from a patient which is indicative of a period of REM sleep with irregular breathing due to phasic REM in a patient.

FIG. 8 shows a period of REM sleep. In this phase of sleep, which occurs, e.g., for 10–30 minutes every 90 minutes of normal sleep, a breathing pattern is often characterized by irregular breathing. This pattern represents a potential exception to the use of irregularity to indicate wakefulness with anxiety. However, during this type of breathing, the patient is asleep and the applied pressure must be maintained (i.e., not reduced as during wakefulness). The type of irregularity seen during REM differs from that seen in wakefulness in several key parameters. This REM associated pattern of breathing may include, e.g., the absence of larger breaths, especially after pauses, generally high respiratory rates and low flow rates, and a tendency for clustering of small breaths. These differences in the pattern of the respiratory airflow signal from those seen during troubled wakefulness allow the separation of these states and can be used to make a change in the applied pressure.

The processing arrangement 24 also collects and records data for each patient. Such data may be collected and entered manually by a technician or automatically by the processing arrangement 24 itself. For example, the technician may monitor the patient's breathing and simultaneously determine whether the patient is awake. Then, when the patient falls asleep, the technician may mark the breathing patterns of this sleeping patient so that the processing arrangement 24 may utilize this data in future determinations as to whether or not the patient is awake. When a database of the patient's breathing characteristics has been built, determinations as to the patient's wakefulness may be made significantly more accurate.

In step 206, the processing arrangement 24 determines whether there has been a change in the patient's state. For example, the processing arrangement 24 may determine if the patient was asleep and has been awakened; or the patient was awake and has fallen asleep. If there has been no change, the processing arrangement 24 continues with the monitoring procedure.

If there has been a change in the patient's state, the processing arrangement 24 adjusts the pressure to correspond to the patient's current state (step 208). For example, if the patient has been awakened and the patient's breathing patterns indicate a period of troubled wakefulness as shown in FIG. 7, the processing arrangement 24 may reduce the applied pressure provided to the patient during such period. This reduction may be a complete elimination of the applied pressure (i.e., the flow generator 22 reduces the flow rate to a level which does not provide any net pressure to the patient in the mask, while maintaining only the minimum sufficient flow through the circuit to the venting arrangement 28 to prevent $CO_2$ buildup), or a partial reduction (i.e., the flow generator 22 produces only the flow sufficient to maintain a reduced portion of the air pressure that it generates while the patient is asleep).

On the other hand, if the patient has fallen asleep, the processing arrangement 24 may instruct the flow control device 25 to elevate the pressure to the level to be applied while the patient is asleep. For example, this may be indicated where the patient's breathing patterns changed from the pattern shown in FIG. 7 to the pattern shown in FIG. 4. In such a case, the processing arrangement 24 should increase the pressure. From that time on, this increased pressure should not be reduced unless one of a plurality of predetermined breathing patterns is detected. For example, the processing arrangement 24 should at least maintain the same pressure or, preferably, increase the pressure if the patient's breathing pattern indicates an event of elevated upper airway resistance and hypopnea as shown in FIG. 5. Also, the pressure should be at least maintained at the same value, or, preferably, increased, if the patient's breathing pattern indicates a repetitive obstructive apnea as shown in FIG. 6, or if the patient shows irregular breathing which suggests he is in REM sleep, as during this type of breathing the patient is asleep and the applied pressure must be maintained at the same level as during other periods of sleep (i.e., not reduced as during wakefulness).

In step 210, the processing arrangement 24 determines whether instructions to disengage the system 1 have been given. If such instructions have been given (e.g., if the patient has pressed a designated button or a preset time limitation has expired), the system 1 shuts down and ends all monitoring and flow generating activities. Otherwise, the system 1 continues with the monitoring procedure of step 204.

One of the advantages of the system 1 according to the present invention is that the pressure supplied to the patient is adjusted (e.g., reduced to zero or a preset low level) when the patient has an irregular breathing pattern that suggests that he is awake and anxious. When breathing is either regular (e.g., suggesting sleep) or shows sleep disorder breathing events, the pressure may be maintained or increased.

It will be apparent to those skilled in the art that various modifications and variations can be made in the structure and the methodology of the present invention without departing from the spirit or scope of the invention. Thus, it is intended that the present invention cover all modifications and variations of this invention which come within the scope of the appended claims and their equivalents.

What is claimed is:

1. A positive airway pressure system for treatment of a sleeping disorder in a patient, comprising:
   a generator supplying airflow and applying a pressure to an airway of a patient;
   a sensor measuring data corresponding to patient's breathing patterns; and
   a processing arrangement analyzing the breathing patterns to determine whether the breathing patterns are indicative of one of the following patient's states: (i) a regular breathing state, (ii) a sleep disorder breathing state, (iii) a REM sleep state and (iv) a troubled wakefulness state, the processing arrangement adjusting the applied pressure as a function of the patient's state,
   wherein, when the breathing patterns indicate state (iv), the processing arrangement sets a target pressure value and controls the generator to adjust the pressure to approach the target pressure value.

2. The system according to claim 1, wherein, when the breathing patterns indicate one of states (i) and (ii) and (iii), the processing arrangement transfers control of the generator to a therapeutic pressure adjustment arrangement.

3. The system according to claim 1, wherein, when the target pressure value is reached, the processor holds the pressure at the target pressure value until the breathing patterns change from a current state to one of states (i) and (ii) and (iii).

4. The system according to claim 1, wherein the processor adjusts the pressure in predetermined increments to approach the target pressure value.

5. The system according to claim 2, wherein the therapeutic pressure adjustment arrangement controls the generator until the breathing patterns indicate state (iv).

6. The system according to claim 2, wherein the therapeutic pressure adjustment arrangement executes a self-titrating algorithm to control the pressure.

7. The system according to claim 1, wherein when the breathing patterns indicate a change from one of states (i), (ii), (iii) to the state (iv), the processing arrangement controls the generator to reduce the pressure.

8. The system according to claim 2, wherein when the breathing patterns indicate a change from state (iv) to one of states (i), (ii) and (iii), the processing arrangement transfers control of the generator to the therapeutic pressure adjustment arrangement which increases the pressure supplied by the generator.

9. A method for treatment of sleeping disorder in a patient using a positive airway pressure, comprising the steps of:
- supplying an airflow to an airway of a patient using a flow generator;
- measuring data corresponding to the patient's breathing patterns;
- analyzing with the processing arrangement the data corresponding to the breathing patterns to determine whether the breathing patterns are indicative of at least one of the following patient states: (i) a regular breathing state, (ii) a sleep disorder breathing state, (iii) a REM sleep state, and (iv) a troubled wakefulness state;
- using the processing arrangement, controlling the generator to adjust the supplied pressure as a function of the patient's state; and
- when the breathing patterns indicate state (iv), controlling the generator to adjust the supplied pressure to approach a target pressure value.

10. The method according to claim 9, further comprising:
when the breathing patterns indicate one of states (i) and (ii) and (iii), transferring control of the generator, by the processing arrangement, to a therapeutic pressure adjustment arrangement.

11. The method according to claim 9, further comprising:
when the target pressure value is reached, maintaining pressure at the target pressure value by the processing arrangement until the breathing patterns change from a current state to one of states (i) and (ii) and (iii).

12. The method according to claim 9, further comprising:
adjusting the pressure in predetermined increments to approach the target pressure value.

13. The method according to claim 10, further comprising:
controlling the generator by the therapeutic pressure adjustment arrangement until the breathing patterns indicate state (iv).

14. The method according to claim 13, wherein controlling step further includes the substep of:
executing a self-titrating algorithm by the therapeutic pressure adjustment arrangement.

15. The method according to claim 9, wherein, when the breathing patterns indicate a change from one of states (i), (ii), (iii) to the state (iv), reducing, by the processing arrangement, the pressure supplied by the generator.

16. The method according to claim 10, wherein, when the breathing patterns indicate a change from state (iv) to one of states (i), (ii) and (iii), increasing, by the therapeutic pressure adjustment arrangement, the pressure supplied by the generator.

* * * * *